United States Patent
Ignatyev et al.

(10) Patent No.: US 9,346,838 B2
(45) Date of Patent: May 24, 2016

(54) PROCESS FOR THE PREPARATION OF TRIS(PERFLUOROALKYL)PHOSPHINE OXIDES AND BIS(PERFLUOROALKYL)PHOSPHINIC ACIDS

(71) Applicant: Merck Patent GmbH, Darmstadt (DE)

(72) Inventors: Nikolai (Mykola) Ignatyev, Duisburg (DE); Karsten Koppe, Marl-Polsum (DE); Walter Frank, Wuppertal (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/409,064

(22) PCT Filed: Jun. 4, 2013

(86) PCT No.: PCT/EP2013/001630
§ 371 (c)(1),
(2) Date: Dec. 18, 2014

(87) PCT Pub. No.: WO2014/005668
PCT Pub. Date: Jan. 9, 2014

(65) Prior Publication Data
US 2015/0141698 A1 May 21, 2015

(30) Foreign Application Priority Data
Jul. 2, 2012 (DE) .......... 10 2012 013 071

(51) Int. Cl.
*C07F 9/53* (2006.01)
*C07F 9/535* (2006.01)

(52) U.S. Cl.
CPC .............. *C07F 9/5304* (2013.01); *C07F 9/53* (2013.01); *C07F 9/535* (2013.01)

(58) Field of Classification Search
CPC ............................ C07F 9/5304; C07F 9/535
See application file for complete search history.

(56) References Cited

U.S. PATENT DOCUMENTS

| 6,264,818 | B1 | 7/2001 | Heider et al. | |
|---|---|---|---|---|
| 7,202,379 | B2 * | 4/2007 | Welz-Biermann et al. | 562/8 |
| 7,576,242 | B2 | 8/2009 | Ignatyev et al. | |
| 2005/0119513 | A1 * | 6/2005 | Ignatyev et al. | 570/144 |
| 2005/0256334 | A1 | 11/2005 | Welz-Biermann et al. | |
| 2007/0128515 | A1 | 6/2007 | Ignatyev et al. | |
| 2012/0330063 | A1 | 12/2012 | Ignatyev et al. | |

FOREIGN PATENT DOCUMENTS

| WO | 00/21969 A1 | 4/2000 |
|---|---|---|
| WO | 03/087020 A1 | 10/2003 |
| WO | 03/087110 A1 | 10/2003 |
| WO | 2005049555 A1 | 6/2005 |
| WO | 2011110281 A1 | 9/2011 |

OTHER PUBLICATIONS

International Search Report from PCT Application No. PCT/EP2013/001630 dated Aug. 29, 2013.
Tariq Mahmood et al. "Comparative Study of Tris(trifluoromethyl)phosphine Oxide, Tris(nonafluorobutyl)phosphine Oxide, and Fluorobis(nonafluorobutyl)phosphine Oxide with Ammonia and Amines" Inorg. Chem. [1988], vol. 27, pp. 2913-2916.
Tariq Mahmood et al. "New Perfiuoroalkylphosphonic and Bis(perfluoroalkyl)phosphinic Acids and Their Precursors" Inorg. Chem. [1986], vol. 25, pp. 3128-3131.
V. Ya. Semenii et al. "Difluorotris(Perfluoralkyl)Phosphoranes" Journal of General Chemistry of the USSR, [1985], vol. 55, No. 12, pp. 2716-2720. (accessed in 2010, from Plenum Publishing Corporation 1986, pp. 2415-2417).
L. M. Yagupol'skii et al. "Electrochemical Fluorination of Trialkylphosphine Oxides" Journal of General Chemistry of the USSR, [1984, vol. 54, No. 4, pp. 780-784. (accessed in 2012 from Plenum Publishing Corporation, pp. 692-695).
Ram Chand Paul "The Preparation of Tristrifluoromethylphosphine Oxide" Journal Chemical Society, [1955], pp. 574-575. (accessed Jul. 11, 2012).
Nikolai Ignat'ev et al. "Electrochemical Fluorination of Trialkylphosphines" Journal of Fluorine Chemistry, [2000], vol. 103, pp. 57-61.
F.W. Bennett et al. "Organometallic and Organometalloidal Fluorine Compounds—Part VII—Trifluoromethyl Compounds of Phosphorus", Journal of American Chemical Society, [1953], pp. 1565-1571. (also published in 1950 and 1951 and accessed on Jul. 11, 2012).
Michaela Gorg et al. "Facile Syntheses of tris(trifluoromethyl)phosphine and difluorotris(trifluoromethyl) phosphorane" Journal of Fluorine Chemistry, [1996], pp. 103-104.

* cited by examiner

*Primary Examiner* — Sudhakar Katakam
(74) *Attorney, Agent, or Firm* — Millen, White, Zelano and Branigan, P.C.

(57) ABSTRACT

The invention relates to a method for producing tris(perfluoroalkyl)phosphine oxides and bis(perfluoroalkyl)phosphinic acids by reacting tris(perfluoroalkyl)difluorophosphorane or bis(perfluoroalkyl)trifluorophosphorane with non-metal oxides, metalloid oxides or organic compounds with basic oxygen residues.

13 Claims, No Drawings

PROCESS FOR THE PREPARATION OF TRIS(PERFLUOROALKYL)PHOSPHINE OXIDES AND BIS(PERFLUOROALKYL)PHOSPHINIC ACIDS

The invention relates to a process for the preparation of tris(perfluoroalkyl)phosphine oxides and bis(perfluoroalkyl)phosphinic acids by reaction of tris(perfluoroalkyl)difluorophosphorane or bis(perfluoroalkyl)trifluorophosphorane with non-metal oxides, semimetal oxides or organic compounds containing basic oxygen residues.

Tris(perfluoroalkyl)phosphine oxides are known starting materials for a multiplicity of interesting compounds, for example for the synthesis of bis(perfluoroalkyl)phosphinic acids [L. M. Yagupol'skii, V. Y. Semenii et al., J. Gen. Chem. USSR 1984, 54, 692-695; V. Y. Semenii, V. A. Stepanov et al., Zh. Obshch. Khim., 1985, 55, 2716-2720; T. Mahmood, J. M. Shreeve, Inorg. Chem., 1986, 25, 3128-3131; T. Mahmood, J-M. Bao et al., Inorg. Chem., 1988, 27, 2913-2916], bis(perfluoroalkyl)phosphinic acid esters [WO 2005/049555 A1], perfluoroalkyl borates or perfluorinated alcohols, such as, for example, $(C_6H_5)_2C(OH)C_2F_5$ [WO 2003/087020 A1].

R. C. Paul, J. Chem. Soc., 1955, 574-575 describes, for example, the synthesis of tris(trifluoromethyl)phosphine oxide by heating tris(trifluoromethyl)-dichlorophosphorane [$(CF_3)_3PCl_2$] with an excess of anhydrous oxalic acid. The disadvantage of this synthesis is the relatively difficult access to tris(trifluoromethyl)dichlorophosphorane.

V. Ya. Semenii et al, Zh. Obshch. Khim, 55, 12, 1985, 2716-2720 describes the synthesis of tris(perfluoroalkyl)phosphine oxides by reaction of difluorotris(perfluoroalkyl)phosphoranes with hexamethyldisiloxane ($[(CH_3)_3Si]_2O$). The disadvantage of this synthesis is the expensive starting material hexamethyldisiloxane and the formation of the highly flammable by-product trimethylsilyl fluoride in double the molar amount. A complicating factor in the synthesis of tris(pentafluoroethyl)phosphine oxide is that this product has a boiling point of 101° C. and the starting material hexamethyldisiloxane has a boiling point of 99-100° C. Removal of even small amounts of starting material by distillation is therefore made more difficult.

WO 2011/110281 describes the preparation of tris(perfluoroalkyl)phosphine oxides by reaction of tris(perfluoroalkyl)difluorophosphoranes with alkaline-earth metal oxides, alkaline-earth metal carbonates, zinc oxide, copper(I) oxide, copper(II) oxide, silver oxide, mercury(II) oxide, cadmium oxide or cadmium carbonate. A disadvantage of this synthesis is the formation of alkaline-earth metal or copper fluoride, which is in very finely divided form, meaning that removal by filtration is made more difficult. Since all reactions with the exception of mercury(II) oxide yield solid fluorides as secondary compound and these are in some cases relatively hard (for example $MgF_2$ having the Mohs hardness 6), use of Teflon-lined reactors is likewise problematic.

It is therefore desirable to have available an economical synthesis of the phosphine oxides described which can be implemented on a large industrial scale in order that this interesting class of starting materials or perfluoroalkylating agents can be prepared in large amounts.

The object of the invention is therefore to develop an improved process for the preparation of tris(perfluoroalkyl)phosphine oxides which meets the requirements of a large-scale industrial economical synthesis and which does not have the disadvantages of the prior art.

This object is achieved in accordance with the invention by a process having the features of claims 1-13.

Surprisingly, it has been found that the tris(perfluoroalkyl)difluorophosphoranes or bis(perfluoroalkyl)trifluorophosphoranes known as starting materials are capable of reacting with non-metal oxides such as $SO_2$, $POCl_3$, $P_4O_{10}$, $CO_2$, $SeO_2$, semimetal oxides such as $SiO_2$ (sand or silica gel as source of $SiO_2$) or organic compounds containing basic oxygen residues, such as triphenylphoshine oxide ($Ph_3PO$), tetramethylurea, ethylene carbonate or dimethyl carbonate and achieving the desired phosphine oxides.

The by-products formed are usually gaseous compounds which can easily be removed. Some of these by-products are interesting compounds for further applications and can optionally be marketed, in particular phosphinic acids.

The invention therefore relates to a process for the preparation of a) compounds of the formula (I)

$$(C_xF_{2x+1})_nP(O)(F)_{3-n} \qquad (I),$$

where x is 1, 2, 3, 4, 5, 6, 7, 8, 9, 10, 11 or 12 and n=2 or 3, or b) of compounds of the formula (I) and compounds of the formula (II)

$$(C_xF_{2x+1})_2P(O)(OH) \qquad (II)$$

where x is 1, 2, 3, 4, 5, 6, 7, 8, 9, 10, 11 or 12, by reaction of compounds of the formula (III)

$$(C_xF_{2x+1})_nP(F)_{5-n} \qquad (III),$$

where x and n have one of the meanings indicated above, with non-metal oxides, semimetal oxides or organic compounds containing basic oxygen residues, where the reaction in accordance with b) is carried out in the presence of water.

In accordance with the invention, preference is given to the preparation of compounds of the formula (I) in which x corresponds to 2, 3, 4, 5 or 6. Accordingly, starting materials of the formula (III) where x denotes 2, 3, 4, 5 or 6 are preferred.

The invention therefore also relates to the process as described above, characterised in that compounds of the formula (III) where x denotes 2, 3, 4, 5 or 6 are employed.

In accordance with the invention, particular preference is given to the preparation of compounds of the formula (I) where x denotes 2, 4 or 6, In accordance with the invention, particular preference is given to the preparation of compounds of the formula (I) where n is equal to 3. Very particular preference is given to the preparation of tris(pentafluoroethyl)phosphine oxide or tris(nonafluorobutyl)phosphine oxide.

The compounds of the formula (III) are commercially available or can be prepared by known processes which are familiar to the person skilled in the art.

The preparation of the compounds of the formula (III) can be prepared, for example, by electrochemical fluorination of suitable starting compounds, as described in V. Ya. Semenii et al, Zh. Obshch. Khim., 55, 12, 1985, 2716-2720, N. Ignatiev et al, J. Fluorine Chem., 103, 2000, 57-61 and WO 00/21969. The corresponding descriptions are hereby incorporated by way of reference and are regarded as part of the disclosure content.

Perfluoroalkylfluorophosphoranes can also be prepared, for example, starting from elemental phosphorus and perfluoroalkyl iodides, based on the description of F. W. Bennett et al, J. Chem. Soc., 1953, 1565-1571 and M. Görg et al, J. Fluorine Chem., 1996, 79, 103-104.

Preferred compounds of the formula (III) are selected from tris(pentafluoroethyl)difluorophosphorane, tris(heptafluoropropyl)difluorophosphorane, tris(nonafluorobutyl)difluorophosphorane, tris(undecafluoropentyl)difluorophosphorane, tris(tridecafluorohexyl)difluorophosphorane. bis(heptafluoropropyl)trifluorophosphorane, bis(nonafluorobutyl)trifluorophosphorane, bis(tridecafluorohexyl)trifluorophosphorane.

In principle, all non-metal oxides, semimetal oxides or organic compounds containing basic oxygen residues can be employed in the process according to the invention. Non-metal oxides are, as is known, oxides of carbon, nitrogen, phosphorus or sulfur, but also selenium, semimetal oxides are oxides of boron, silicon, arsenic or tellurium. Non-metal oxofluorides of commercial interest are $COF_2$, $P(O)F_3$, $S(O)F_2$ The said organic oxo compounds, and the non-metal or semimetal oxides, as described above, can be used in equimolar amount or large excess.

Non-metal oxides which are preferably used for the purposes of the invention are $SO_2$, $POCl_3$, $P_4O_{10}$, $CO_2$, $SeO_2$, in particular $SO_2$, $CO_2$ and $SeO_2$.

A semimetal oxide which is preferably used for the purposes of the invention is $SiO_2$.

Organic compounds containing basic oxygen residues which are preferably used for the purposes of the invention are triphenylphoshine oxide ($Ph_3PO$), ethylene carbonate or dimethyl carbonate, in particular ethylene carbonate.

For the synthesis of the compounds of the formula (I), as described above, an embodiment of the invention is preferred in which non-metal oxides and semimetal oxides are employed, in particular the compounds mentioned as preferred. The invention therefore relates to a process, as described above, characterised in that non-metal oxides and semimetal oxides are used. Particular preference is given to the use of silicon dioxide, selenium dioxide or sulfur dioxide.

The reaction times can be reduced significantly if small amounts of water are added. Water can be added here in a molar proportion of 0.01 to 0.8 equivalents. 0.1 to 0.5 equivalents of water are preferably added. Due to the addition of relatively large amounts of water, preferably 0.5 to 1.0 equivalents of water, some of the product reacts further to give the corresponding bis(perfluoroalkyl)phosphinic acids of the formula (II) and some of the starting material reacts to give tris(perfluoroalkyl)trifluorophosphate.

Bis(perfluoroalkyl)phosphinic acids can be separated from tris(perfluoroalkyl)phosphine oxides by distillation.

The solids employed in the process according to the invention should preferably be employed in the ground state in order that the largest possible surface is present for the reaction. Any type of grinding is possible, for example grinding by means of a ball mill.

The solids do not require drying of any type. In general, the proportion of water described results in acceleration of the reaction.

The reaction can in principle take place at temperatures between 80° C. and 200° C. If low reaction temperatures are selected, the corresponding reaction time is longer. The invention therefore also relates to a process, as described above, characterised in that the reaction takes place at temperatures between 25° C. and 200° C.

The reaction is preferably carried out at room temperature if long reaction times in the order of days are desired.

The reaction is preferably carried out at reaction temperatures of 50° C. to 180° C., particularly preferably at reaction temperatures of 80° C. to 150° C. The temperature indications in the example part here relate to the reaction temperature of the heating medium used.

The reaction can be carried out in a glass apparatus or in an apparatus made of plastic (such as, for example, Teflon) or steel.

The reaction in the plastic apparatus or in the steel apparatus generally takes longer.

The reaction is preferably carried out without solvents. However, it is also possible to carry out the reaction in the presence of solvents which are inert to the compounds of the formula (I), (II) and (III), for example dialkyl ethers containing alkyl groups of 2 to 4 C atoms, for example diethyl ether, diisopropyl ether, dipropyl ether, methyl butyl ether.

The by-products formed are gaseous and can easily be removed. Reactions in which solids were used can, for example, be removed simply by filtration or decantation or condensed off or distilled off in vacuo.

Isolation of the products is not necessary in the case of gaseous reactants. The by-products are discharged constantly on use of cooling above the boiling point of the by-products. The residue is principally product.

However, the compounds of the formula (I) can also be separated off by condensation or distillation from solid by-products formed.

The compounds of the formula (I) prepared by the process according to the invention, as described above, are pure compounds and are ideally suited for further reaction, in particular for hydrolysis using water for the preparation of bis(perfluoroalkyl)phosphinic acids of the formula (II) and/or perfluoroalkylphosphonic acids.

Even without further comments, it is assumed that a person skilled in the art will be able to utilise the above description in the broadest scope. The preferred embodiments and examples should therefore merely be regarded as descriptive disclosure which is absolutely not limiting in any way.

EXAMPLES

NMR Spectroscopy

NMR samples are measured at 25° C. either in a 5 mm ($\varnothing_A$) glass NMR tube or in a 3.7 mm ($\varnothing_A$) FEP inliner. In the case of measurements in FEP, the inliner is introduced into a 5 mm ($\varnothing_A$) glass NMR tube. The locking agent ($CD_3CN$) is thus located in the glass NMR tube between glass and FEP inliner. The measurements are carried out on a 400 MHz Bruker Avance III spectrometer with a 9.3980 T cryomagnet and a 5 mm BBFO probe head.

$^1H$ NMR spectra are measured in the $^1H/^{19}F$ channel at 400.17 MHz. $^{13}C$, $^{19}F$ and $^{31}P$ NMR spectra were measured in the broadband channel at 100.62, 376.54 and 161.99 MHz. The $^1H$ NMR chemical shifts are relative to tetramethylsilane (TMS) and give rise to the chemical shifts indicated in brackets for the solvents $CDCl_3$ (7.24 ppm) and $CD_3CN$ (1.95 ppm). The $^{13}C$ chemical shifts are likewise relative to TMS and give rise to the chemical shifts indicated in brackets for the solvents $CDCl_3$ (77.2 ppm) and $CD_3CN$ (118.7 ppm). The $^{19}F$ chemical shifts are relative to $CFCl_3$ and give rise to the chemical shifts indicated in brackets for the internal standards $C_6F_6$ (−162.9 ppm) or $C_6H_5CF_3$ (−63.9 ppm). The $^{31}P$ chemical shifts are relative to $H_3PO_4$ (85%).

Chemicals Used:

Tris(pentafluoroethyl)difluorophosphorane and tris(nonafluorobutyl)difluorophosphorane are prepared as described in WO 00/21969.

Example 1

Preparation of tris(pentafluoroethyl)phosphine oxide, $(C_2F_5)_3P=O$, by reaction of tris(pentafluoroethyl)difluorophosphorane with carbon dioxide

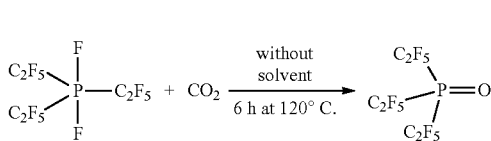

12.01 g (28.0 mmol) of tris(pentafluoroethyl)difluorophosphorane, $(C_2F_5)_3PF_2$, are initially introduced in a 100 ml glass round-bottomed flask and warmed (120° C. oil-bath temperature). A cooled (−30° C. to −35° C.) intensive reflux condenser is connected downstream of the flask. A 250 ml glass round-bottomed flask containing dry ice is connected via a T-piece so that gaseous $CO_2$ is forced through the phosphorane liquid. The liquid is stirred at 120° C. for 6 h. In this time, a total of about 400 g (9 mol) of $CO_2$ are bubbled through the hot liquid. After 6 h, the condenser temperature is warmed to −5° C. The clear and colourless liquid remaining (4.53 g) consists of $(C_2F_5)_3PF_2$ (49%), $(C_2F_5)_3P=O$ (49%) and $(C_2F_5)_2P(O)OH$ (2%). Tris(pentafluoroethyl)phosphine oxide, $(C_2F_5)_3P=O$, is isolated from the reaction mixture by distillation.

The product, $(C_2F_5)_3P=O$, is characterised by means of $^{19}F$ and $^{31}P$ NMR spectra. (in $CD_3CN$, in ppm)

$^{19}F$ NMR: −82.1 s (9F), −119.6 d (6F), $^2J_{F,P}$=84 Hz $^{31}P$ NMR: 18.5 sep (1P), $^2J_{F,P}$=84 Hz Example 2

Preparation of tris(pentafluoroethyl)phosphine oxide, $(C_2F_5)_3P=O$, by reaction of tris(pentafluoroethyl)difluorophosphorane with silicon dioxide (sand)

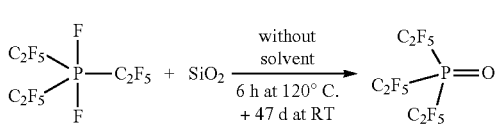

3.03 g (50.3 mmol) of fire-extinguishing sand as $SiO_2$ source are added to 18.21 g (42.7 mmol) of tris(pentafluoroethyl)difluorophosphorane, $(C_2F_5)_3PF_2$, in a 100 ml glass round-bottomed flask and warmed (120° C. oil-bath temperature). An intensive reflux condenser is connected downstream of the flask. The suspension is stirred at 120° C. for 6 h. Conversion to $(C_2F_5)_3P=O$ of 8% can be detected. The entire suspension is left to stand at room temperature for a further 47 d, after which the conversion to $(C_2F_5)_3P=O$ increases to 68%. The product mixture can be separated by distillation at atmospheric pressure or condensation in vacuo. The product, $(C_2F_5)_3P=O$, is characterised by means of $^{19}F$ and $^{31}P$ NMR spectra and gives comparable values to Example 1.

Example 3

Preparation of tris(pentafluoroethyl)phosphine oxide, $(C_2F_5)_3P=O$, by reaction of tris(pentafluoroethyl)difluorophosphorane with silicon dioxide in the presence of water

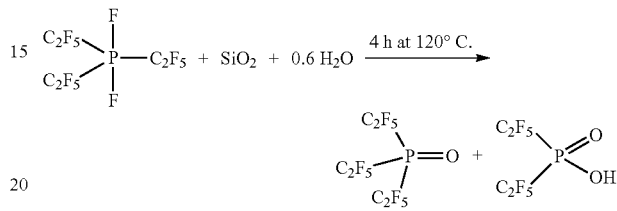

0.30 g (16.7 mmol) of water and 3.19 g (53.1 mmol) of fire-extinguishing sand as $SiO_2$ source are added to 12.0 g (28.0 mmol) of tris(pentafluoroethyl)difluorophosphorane, $(C_2F_5)_3PF_2$, in a 100 ml glass round-bottomed flask and warmed (20° C. oil-bath temperature). An intensive reflux condenser is connected downstream of the flask. The suspension is stirred at 120° C. for 4 h. Complete consumption of $(C_2F_5)_3PF_2$ and formation of $(C_2F_5)_3P=O$ (72.0%) and $(C_2F_5)_2P(O)OH$ (28.0%) can be detected. The entire suspension is condensed at room temperature in vacuo ($10^{-3}$ mbar). Clear and colourless $(C_2F_5)_3P=O$ (6.27 g; 15.5 mmol; 55%) can be isolated in 99% purity. Further $(C_2F_5)_3P=O$ can be isolated from the solid residue by extraction.

The product, $(C_2F_5)_3P=O$, is characterised by means of $^{19}F$ and $^{31}P$ NMR spectra and gives comparable values to Example 1.

Example 4

Preparation of tris(pentafluoroethyl)phosphine oxide, $(C_2F_5)_3P=O$, by reaction of tris(pentafluoroethyl)difluorophosphorane with sulfur dioxide

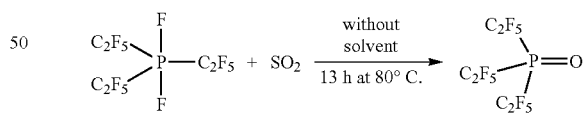

14.45 g (33.9 mmol) of tris(pentafluoroethyl)difluorophosphorane, $(C_2F_5)_3PF_2$, are initially introduced in a 100 ml glass round-bottomed flask. A cooled (−80° C.) condensation condenser is connected downstream of the flask. Liquid $SO_2$ (about 5 ml), which is slowly released into the system, is via a T-piece connected in between with connected Young trap. The emulsion is stirred at −0° C. for 3 h before the intensive condenser is slowly warmed to room temperature in order to discharge excess $SO_2$ in gaseous form. After this time, $(C_2F_5)_3PF_2$ (99%) and $(C_2F_5)_3P=O$ (1%) can be detected. On the next day, $SO_2$ is again condensed into the same apparatus and again stirred at 80° C. for 5 h. After this time, $(C_2F_5)_3PF_2$ (37%) and $(C_2F_5)_3P=O$ (63%) can be detected.

Again on the next day, $SO_2$ is again condensed into the same apparatus and again stirred at 80° C. for 8 h. After this time, $(C_2F_5)_3PF_2$ (18%) and $(C_2F_5)_3P=O$ (82%) can be detected.

The product mixture can be separated by distillation at atmospheric pressure or condensation in vacuo.

The product, $(C_2F_5)_3P=O$, is characterised by means of $^{19}F$ and $^{31}P$ NMR spectra and gives comparable values to Example 1.

Example 5

Preparation of tris(nonafluorobutyl)phosphine oxide, $(C_4F_9)_3P=O$, by reaction of tris(nonafluorobutyl) difluorophosphorane with sulfur dioxide

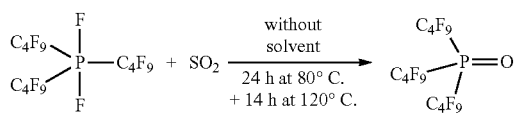

15.21 g (20.9 mmol) of tris(nonafluorobutyl)difluorophosphorane, $(C_4F_9)_3PF_2$, are initially introduced in a 100 ml glass round-bottomed flask and warmed (80° C. oil-bath temperature). A cooled (−30° C. to −35° C.) intensive reflux condenser is connected downstream of the flask. Liquid $SO_2$ (about 5 ml), which is slowly released into the system, is via a T-piece connected in between with connected Young trap. The emulsion is stirred at 80° C. for 24 h before the intensive condenser is warmed to 0° C. in order to discharge excess $SO_2$ in gaseous form. After this time, conversion to $(C_4F_9)_3P=O$ of 12% can be detected. $SO_2$ (about 5 ml) is again condensed in and again stirred at 120° C. for 14 h. After this time, a conversion to $(C_4F_9)_3P=O$ of 70% can be detected. Separation of $(C_4F_9)_3P=O$ and $(C_4F_9)_3PF_2$ can be carried out by condensation at 70° C. in vacuo ($10^{-3}$ mbar). The product, $(C_4F_9)_3P=O$, is characterised by means of $^{19}F$ and $^{31}P$ NMR spectra. (in $CD_3CN$, in ppm):
$^{19}F$ NMR: −84.0 t (9F), $^3J_{F,F}$=9 Hz, −114.3 d (6F), $^2J_{F,P}$=86 Hz, −120.7 s (6F), −125.8 s (6F)
$^{31}P$ NMR: 22.7 sep, $^2J_{F,P}$=86 Hz

Example 6

Preparation of tris(nonafluorobutyl)phosphine oxide, $(C_4F_9)_3P=O$, by reaction of tris(nonafluorobutyl) difluorophosphorane with sulfur dioxide in the presence of water

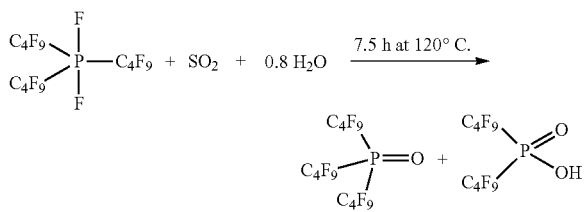

0.28 g (15.5 mmol) of water is added to 14.04 g (19.3 mmol) of tris(nonafluorobutyl)difluorophosphorane, $(C_4F_9)_3PF_2$, in a 100 ml glass round-bottomed flask and warmed (120° C. oil-bath temperature). A cooled (−30° C. to −35° C.) intensive reflux condenser is connected downstream of the flask. Liquid $SO_2$ (about 5 ml), which is slowly released into the system, is via a T-piece connected in between with connected Young trap. The emulsion is stirred at 120° C. for 7.5 h before the intensive condenser is warmed to −5° C. in order to discharge excess $SO_2$ in gaseous form. Virtually complete consumption (98.4%) of $(C_4F_9)_3PF_2$ and formation of $(C_4F_9)_3P=O$ (78.0%), $(C_4F_9)_2P(O)OH$ (14.0%) can be detected. The entire suspension is condensed at 75° C. in vacuo ($10^{-3}$ mbar). Clear and colourless $(C_4F_9)_3P=O$ (8.81 g; 12.5 mmol; 79%) can be isolated in 92% purity. Pure, crystalline, clear and colourless $(C_4F_9)_2P(O)OH$ can be isolated from the solid residue by sublimation at 75° C. in vacuo ($10^{-3}$ mbar).

Both $(C_4F_9)_3P=O$ and also $(C_4F_9)_2P(O)OH$ are characterised by means of $^{19}F$ and and $^{31}P$ NMR spectra. The $^{19}F$ and $^{31}P$ NMR spectra for $(C_4F_9)_3P=O$ give comparable values to Example 5.

NMR spectra for $(C_4F_9)_2P(O)OH$ (in $CD_3CN$, in ppm)
$^{19}F$ NMR: −81.8 t (6F), $^3J_{F,F}$=9 Hz, −121.4 s (4F), −122.4 d (4F), $^2J_{F,P}$=79 Hz, −126.6 s (4F)
$^{31}P$ NMR: 4.7 sep, $^2J_{F,P}$=79 Hz

Example 7

Preparation of tris(pentafluoroethyl)phosphine oxide, $(C_2F_5)_3P=O$, by reaction of tris(pentafluoroethyl) difluorophosphorane with selenium dioxide

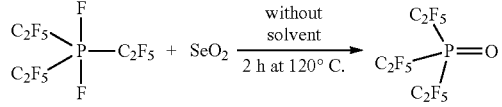

1.43 g (12.9 mmol) of selenium dioxide, $SeO_2$, are added to 6.50 g (15.3 mmol) of tris(pentafluoroethyl)difluorophosphorane, $(C_2F_5)_3PF_2$, in a 100 ml glass round-bottomed flask and warmed (110° C. oil-bath temperature). An intensive reflux condenser is connected downstream of the flask. The suspension is stirred at 110° C. for 2 h. Complete consumption of $(C_2F_5)_3PF_2$ and formation of $(C_2F_5)_3P=O$ (94%) can be detected. 4.642 g (11.5 mmol) of $(C_2F_5)_3P=O$ (yield 89%) having a purity of 94% can be isolated by simple decantation.

The product, $(C_2F_5)_3P=O$, is characterised by means of $^{19}F$ and $^{31}P$ NMR spectra and gives comparable values to Example 1.

Example 8

Preparation of tris(nonafluorobutyl)phosphine oxide, $(C_4F_9)_3P=O$, by reaction of tris(nonafluorobutyl) difluorophosphorane with selenium dioxide

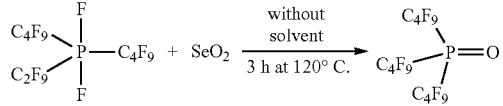

2.14 g (19.3 mmol) of selenium dioxide, $SeO_2$, are added to 12.445 g (17.1 mmol) of tris(nonafluorobutyl)difluorophosphorane, $(C_4F_9)_3PF_2$, in a 100 ml glass round-bottomed flask and warmed (120° C. oil-bath temperature). An intensive reflux condenser is connected downstream of the flask. The suspension is stirred at 120° C. for 3 h. After this time, no weight loss, but complete consumption of $(C_4F_9)_3PF_2$ and formation of $(C_4F_9)_3P=O$ can be detected. The entire suspension is condensed at 80° C. in vacuo ($10^{-3}$ mbar). Clear and colourless $(C_4F_9)_3P=O$ (7.426 g; 10.5 mmol; 62%) in 87% purity can be isolated.

The product, $(C_4F_9)_3P=O$, is characterised by means of $^{19}F$ and $^{31}P$ NMR spectra and gives comparable values to Example 5.

Example 9

Preparation of bis(pentafluoroethyl)phosphinyl fluorides, $(C_2F_5)_2P(O)F$, by reaction of bis(pentafluoroethyl)trifluorophosphorane with sulfur dioxide

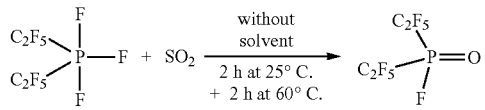

4.46 g (13.7 mmol) of bis(pentafluoroethyl)trifluorophosphorane, $(C_2F_5)_2PF_3$, are initially introduced in a 100 ml glass round-bottomed flask with dropping funnel and condensation condenser (−80° C.) and cooled to 0° C. $SO_2$ (about 3 ml) is condensed into this clear and colourless liquid. The emulsion is warmed to 25° C. and stirred at 25° C. for 2 h and at 60° C. (bath temperature) for 2 h. The condensation condenser is subsequently slowly warmed to room temperature in order to discharge excess $SO_2$ in gaseous form. The residue contains $(C_2F_5)_2P(O)F$, which is detected by NMR spectroscopy.

Bis(pentafluoroethyl)phosphinyl fluorides, $(C_2F_5)_2P(O)F$, is isolated from the reaction mixture by distillation.

The product, $(C_2F_5)_2P(O)F$, is characterised by means of $^{19}F$ and $^{31}P$ NMR spectra (in $CD_3CN$, in ppm):

$^{19}F$ NMR: −81.6 d, m (1F), $^1J_{P,F}$=1204 Hz, −80.7 m (6F), −123.2 m (4F)

$^{31}P$ NMR: 22.7 d, t, t, $^1J_{F,P}$=1204 Hz, $^2J_{F,P}$=107 Hz, $^2J_{F,P}$=95 Hz

The invention claimed is:

1. A process for the preparation of compounds of formula (I)

$$(C_xF_{2x+1})_nP(O)(F)_{3-n} \quad (I)$$

or of compounds of the formula (I) and compounds of formula (II)

$$(C_xF_{2x+1})_2P(O)(OH) \quad (II)$$

where, in the formulae (I) and (II), x is 1, 2, 3, 4, 5, 6, 7, 8, 9, 10, 11 or 12 and n=2 or 3, comprising reacting at least compounds of formula (III)

$$(C_xF_{2x+1})_nP(F)_{5-n} \quad (III),$$

where x and n have one of the meanings indicated above, with non-metal oxides, semimetal oxides or organic compounds containing basic oxygen residues, said compounds containing basic oxygen residues being triphenylphoshine oxide ($Ph_3PO$), tetramethylurea, ethylene carbonate or dimethyl carbonate, where the reaction is optionally carried out in the presence of water.

2. The process according to claim 1, wherein compounds of the formula (III) where x denotes 2, 3, 4, 5 or 6 are employed.

3. The process according to claim 1, wherein compounds of the formula (II) are tris(pentafluoroethyl) difluorophosphorane, tris (heptafluoropropyl) difluorophosphorane, tris(nonafluorobutyl) difluorophosphorane, tris (undecafluoropentyl) difluorophosphorane, tris (tridecafluorohexyl) difluorophosphorane, bis (heptafluoropropyl) trifluorophosphorane, bis (nonafluorobutyl) trifluorophosphorane or bis (tridecafluorohexyl) trifluorophosphorane.

4. The process according to claim 1, wherein non-metal oxides or semimetal oxides are used.

5. The process according to claim 1, wherein $SO_2$, $POCl_3$, $P_4O_{10}$, $CO_2$ or $SeO_2$ is used.

6. The process according to claim 1, wherein $SO_2$, $CO_2$ or $SeO_2$ is used.

7. The process according to claim 1, wherein $SiO_2$ is used.

8. The process according to claim 1, wherein ethylene carbonate is used.

9. The process according to claim 1, wherein n is equal to 3.

10. The process according to claim 1, carried out in the presence of water.

11. The process according to claim 1, carried out in the presence of at least one organic solvent.

12. The process according to claim 1, wherein the reaction takes place at temperatures between 25° C. and 200° C.

13. The process according to claim 1, wherein the reaction takes place at room temperature.

* * * * *